(12) United States Patent
Chinea et al.

(10) Patent No.: US 8,080,097 B2
(45) Date of Patent: Dec. 20, 2011

(54) SYSTEM AND A METHOD FOR THE CREATION OF EDIBLE, OPTICALLY INVISIBLE IMAGES

(75) Inventors: Vanessa I. Chinea, Isabela, PR (US); Marcos A. Barreto, Aguadilla, PR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1682 days.

(21) Appl. No.: 10/946,883

(22) Filed: Sep. 22, 2004

(65) Prior Publication Data

US 2005/0099476 A1 May 12, 2005

Related U.S. Application Data (63) Continuation-in-part of application No. 10/703,697, filed on Nov. 6, 2003, now Pat. No. 7,166,154.

(51) Int. Cl.
*B41M 3/14* (2006.01)
*A61K 9/28* (2006.01)
*A61K 9/44* (2006.01)
*B44F 1/00* (2006.01)
*C09D 11/00* (2006.01)

(52) U.S. Cl. .......... 106/31.13; 106/31.14; 106/31.15; 424/10.1; 424/10.2; 424/10.3; 427/2.14; 427/2.23; 427/7; 283/72; 283/74

(58) Field of Classification Search .......... 427/2.1, 427/2.14, 2.23, 7; 424/10.1–10.3; 106/31.13–31.15; 283/72, 74
See application file for complete search history.

(56) References Cited

U.S. PATENT DOCUMENTS

| | | | |
|---|---|---|---|
| 5,006,362 A * | 4/1991 | Hilborn ............... 427/2.23 |
| 5,271,764 A | 12/1993 | Winnik et al. |
| 5,286,286 A | 2/1994 | Winnik et al. |
| 5,421,869 A * | 6/1995 | Gundjian et al. ........ 106/31.19 |
| 5,541,633 A | 7/1996 | Winnik et al. |
| 5,837,042 A * | 11/1998 | Lent et al. ............. 106/31.14 |
| 6,183,466 B1 * | 2/2001 | Wong et al. ............. 604/892.1 |
| 6,312,960 B1 | 11/2001 | Balch et al. |
| 6,336,708 B1 | 1/2002 | West et al. |
| 6,501,825 B2 * | 12/2002 | Kaiser et al. .............. 378/45 |
| 6,559,306 B2 | 5/2003 | Kaul et al. |
| 6,667,394 B2 | 12/2003 | Pease et al. |
| 2003/0032046 A1 | 2/2003 | Duffy et al. |
| 2003/0087239 A1 | 5/2003 | Stanton et al. |
| 2003/0100637 A1 | 5/2003 | Mimura et al. |
| 2003/0129618 A1 | 7/2003 | Moronne et al. |

(Continued)

FOREIGN PATENT DOCUMENTS

GB   2 074 947   11/1981

(Continued)

OTHER PUBLICATIONS

Practical Guidebook for The Japanese Pharmacopoeia (Thirteenth Edition), First Section, Particulars on Medicinal Chemicals, "NI" row (First Section, Particulars on Medicinal Chemicals. "A" row. Hirokawa Shoten Co., Satsuo Hirokawa, 1998, First Edition).

*Primary Examiner* — Timothy Meeks
*Assistant Examiner* — Cachet Sellman (57) ABSTRACT

A method for labeling a UV-fluorescing substrate includes positioning a UV-fluorescing substrate adjacent to an inkjet material dispenser, and selectively jetting an edible, invisible, non-UV fluorescing ink onto the UV-fluorescing substrate with the inkjet material dispenser.

66 Claims, 8 Drawing Sheets

U.S. PATENT DOCUMENTS

| | | |
|---|---|---|
| 2003/0143268 A1 | 7/2003 | Lewis et al. |
| 2003/0170392 A1 | 9/2003 | Chari et al. |
| 2003/0224361 A1 | 12/2003 | Qiao et al. |
| 2003/0232343 A1 | 12/2003 | Leproust et al. |

FOREIGN PATENT DOCUMENTS

| | | | |
|---|---|---|---|
| GB | 2074947 A | * | 11/1981 |
| JP | 53-056315 | | 5/1978 |
| JP | 6-157558 | | 6/1994 |
| JP | 8-166349 | | 6/1996 |
| JP | 09-059145 | | 3/1997 |
| JP | 9-509372 | | 9/1997 |
| JP | 11-199480 | | 7/1999 |
| JP | 2000-515920 | | 11/2000 |
| JP | 2000515920 | * | 11/2000 |
| JP | 2001-507052 | | 5/2001 |
| JP | 2001507052 | * | 5/2001 |
| JP | 2002-187857 | | 7/2002 |
| JP | 2003-082263 | | 3/2003 |
| JP | 2003082263 A | * | 3/2003 |
| JP | 2004217841 A | * | 8/2004 |
| WO | WO-9812560 | | 3/1998 |

* cited by examiner

SYSTEM AND A METHOD FOR THE CREATION OF EDIBLE, OPTICALLY INVISIBLE IMAGES

RELATED APPLICATIONS

The present application is a Continuation-in-Part and claims priority under 35 U.S.C. § 120 of U.S. patent application Ser. No. 10/703,697, now U.S. Pat. No. 7,166,154 filed Nov. 6, 2003, by Marcos A. Barreto, entitled "A System and a Method for an Edible, Optically Invisible Ink."

BACKGROUND

Pharmaceutical products such as pills and capsules traditionally include a number of markings. Marks or printed information on pharmaceutical products typically include information such as logos, names, or bar codes that may be used to identify the type, dosage, and/or source of the pharmaceuticals. These markings also aid in the dispensing and administration of pharmaceuticals to patients.

In order to mark or otherwise label pharmaceutical products such as pills and capsules, the methodology has to be approved by the food and drug administration (FDA). The FDA has a number of lists containing approved colorants and labels that may be used to mark or otherwise label pharmaceutical products.

Traditional methods of marking pharmaceutical products such as pills and capsules include coloring the pharmaceutical products with FDA certified colorants, altering the surface appearance of the pharmaceutical products through engravings, applying an FDA approved label to the surface of the pharmaceutical products, or painting the pharmaceutical product.

While traditional methods are somewhat effective in marking or otherwise distinguishing pharmaceutical products, traditional methods of marking pharmaceutical products significantly compromise the outward appearance of the pharmaceutical products. Additionally, traditional methods do little to facilitate the control of counterfeit production and fraudulent dispensing of pharmaceuticals, since these outer markings are easily identifiable and reproducible. Moreover, a majority of the traditional methods and formulations for marking or otherwise labeling pharmaceutical products necessitate contact with the pharmaceutical. Any such contact with the pharmaceutical products increases the likelihood of causing physical or chemical damage to the pharmaceutical product.

SUMMARY

A method for labeling a UV-fluorescing substrate includes positioning a UV-fluorescing substrate adjacent to an inkjet material dispenser, and selectively jetting an edible, invisible, non-UV fluorescing ink onto the UV-fluorescing substrate with the inkjet material dispenser.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

An exemplary system and method for implementing an edible, invisible ink is disclosed herein. More specifically, a system and a method are disclosed that may be used in the creation of printed images (letters, figures, drawings, bar codes) that are invisible to white light illumination but visible in ultraviolet light illumination. According to one exemplary embodiment, the printed images are created by printing an edible, invisible, non-UV fluorescing solution or drug formulation on a fluorescent edible media using ink jet technology. When an ultraviolet light is applied to the media, the fluorescent edible media fluoresces while the non-UV fluorescent solution or drug formulation does not. This difference in fluorescence between the printed drug solution and the media produces visible images equivalent to those traditionally seen under "white" light illumination. Additionally, the invisible, non-fluorescing ink is non-toxic, edible, and made of compounds listed in the Generally Regarded as Safe (GRAS) list sponsored by the Food and Drug Administration (FDA).

As used in the present specification and the appended claims, the term "edible" is meant to be understood broadly as any composition that is suitable for human consumption and is non-toxic. Similarly, the phrase "edible ink" is meant to be understood broadly as any jettable fluid, regardless of whether it contains a dye or other colorant that is suitable for human consumption and complies with applicable standards such as food, drug, and cosmetic (FD&C) regulations in the United States and/or Eurocontrol experimental centre (E.E.C.) standards in the European Union. Additionally, the term "invisible" is meant to be understood broadly as meaning any image, color, or shading that, when viewed by the naked eye under traditional white light conditions, is not prominent or readily noticeable. The term "jettable" is meant to be understood both in the present specification and in the appended claims as any material that may be selectively deposited by any digitally addressable inkjet material dispenser.

In the following description, for purposes of explanation, numerous specific details are set forth in order to provide a thorough understanding of the present system and method for creating edible, optically invisible images. It will be apparent, however, to one skilled in the art, that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Structure

Figure 1:
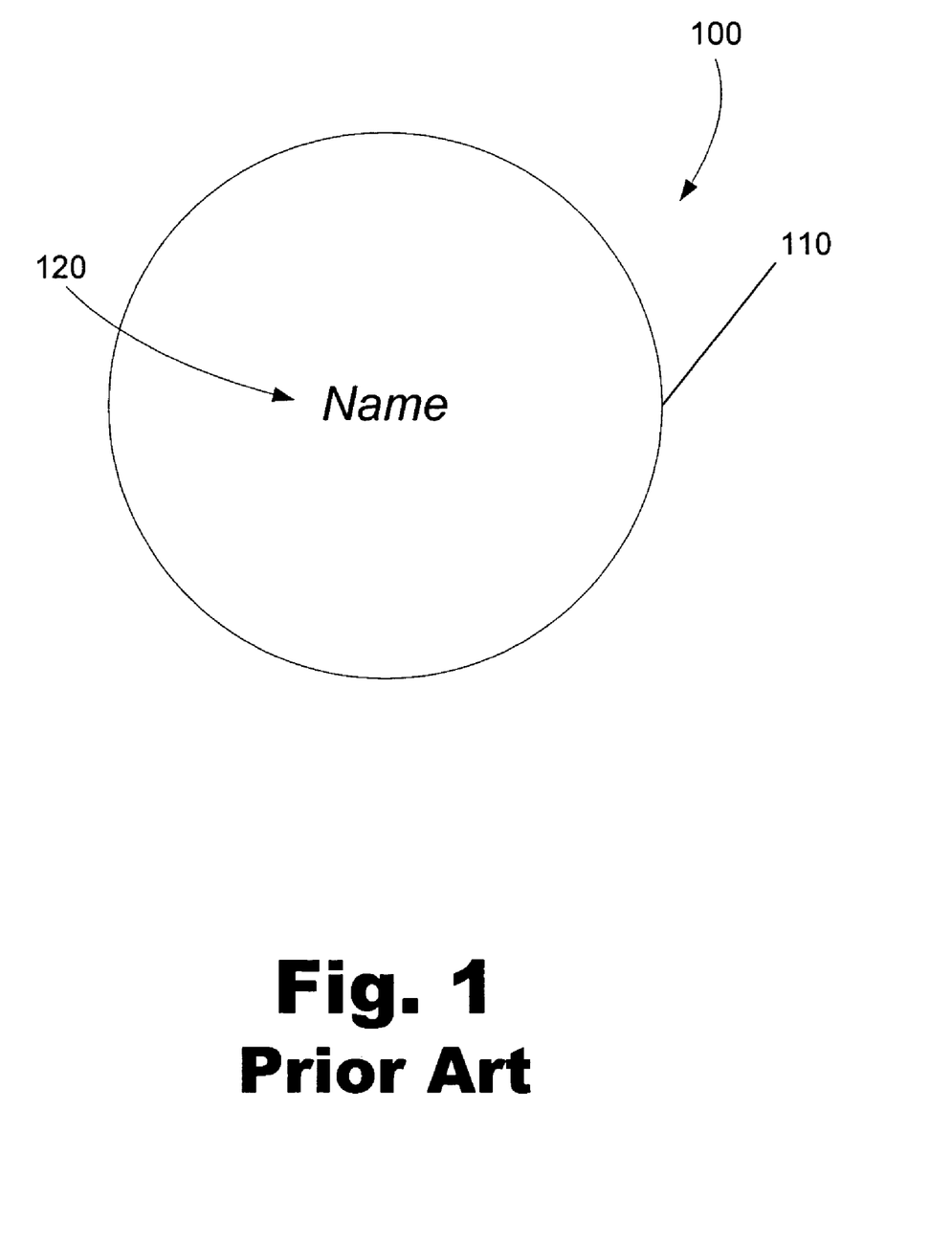
FIG. 1 is a perspective view of a pharmaceutical product labeled according to teachings of the prior art.

FIG. 1 illustrates a traditionally marked pharmaceutical product (100). As shown in FIG. 1, the pharmaceutical product (100) includes a pill (110) having a product name (120) printed thereon. As shown in FIG. 1, the product name (120) or other surface markings compromise the outward appearance of the pharmaceutical product (100).

Figure 2:
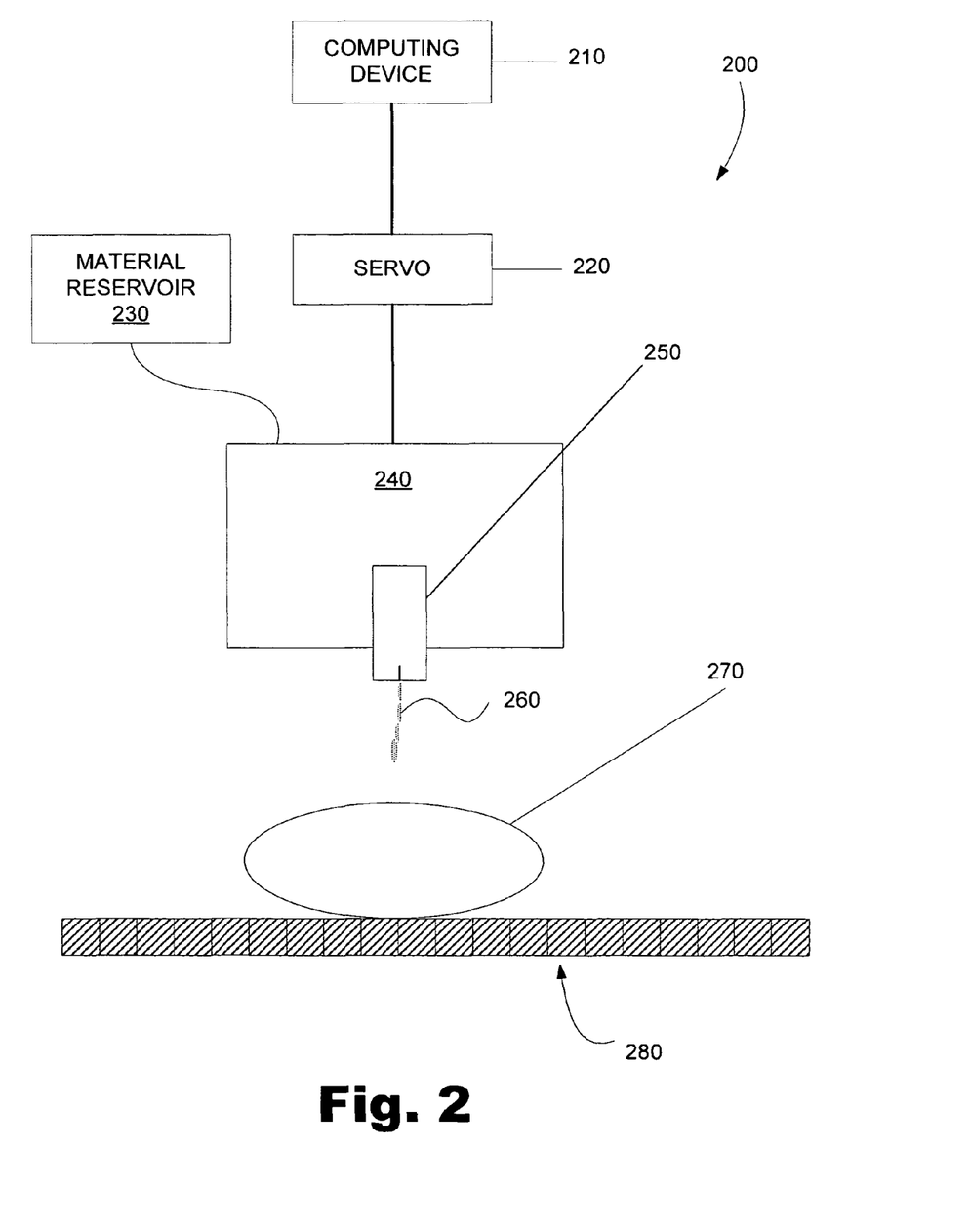
FIG. 2 is a simple block diagram illustrating a system that may be used to implement exemplary embodiments of the present system and method.

FIG. 2 illustrates an exemplary system (200) that may be used to form an edible and optically invisible image on a pharmaceutical product (270) or other substrate. As illustrated in FIG. 2, a non-UV illuminating ink composition (260) may be applied to a pharmaceutical product (270) according to one exemplary embodiment. As shown in FIG. 2, the present system includes a computing device (210) controllably coupled through a servo mechanism (220) to a moveable carriage (240) having an inkjet dispenser (250) disposed thereon. A material reservoir (230) is also coupled to the moveable carriage (240), and consequently to the inkjet print head (250). A substrate (280) is located adjacent to the inkjet dispenser (250) having a pharmaceutical product (270) disposed thereon. While the present embodiment is described, for ease of explanation only, in the context of marking a pharmaceutical product (270) with an edible, non-UV illuminating ink (260), the present system and method may be used to form an edible, optically invisible image using the present non-UV illuminating ink (260) on any number of products including, but in no way limited to, food products, dental products, etc. Moreover, the present system and method may be further extended to the pharmaceutical field by replacing the pharmaceutical product (270) with an edible, UV illuminating wafer configured to receive a non-UV illuminating ink containing a precise dosage of a pharmaceutical. The above-mentioned components of the present system will now be described in further detail below.

The computing device (210) that is controllably coupled to the servo mechanism (220), as shown in FIG. 2, controls the selective deposition of an edible, non-UV illuminating ink (260) on the pharmaceutical product (270). A representation of a desired image or label may be formed using a program hosted by the computing device (210). That representation may then be converted into servo instructions that are housed in a processor readable medium (not shown). When accessed by the computing device (210), the instructions housed in the processor readable medium may be used to control the servo mechanisms (220) as well as the movable carriage (240) and inkjet dispenser (250). The computing device (210) illustrated in FIG. 2 may be, but is in no way limited to, a workstation, a personal computer, a laptop, a personal digital assistant (PDA), or any other processor containing device.

The moveable carriage (240) of the present printing system (200) illustrated in FIG. 2 is a moveable material dispenser that may include any number of inkjet material dispensers (250) configured to dispense the present edible, non-UV illuminating ink (260). The moveable carriage (240) may be controlled by the computing device (210) and may be controllably moved by, for example, a shaft system, a belt system, a chain system, etc. making up the servo mechanism (220). As the moveable carriage (240) operates, the computing device (210) may inform a user of operating conditions as well as provide the user with a user interface.

As an edible, optically invisible image made of a non-UV illuminating substance is printed on a pharmaceutical product (270), the computing device (210) may controllably position the moveable carriage (240) and direct one or more of the inkjet dispensers (250) to selectively dispense the edible, non-UV illuminating ink at predetermined locations on the pharmaceutical product (270) as digitally addressed drops, thereby forming the desired optically invisible image. The inkjet material dispensers (250) used by the present printing system (100) may be any type of inkjet dispenser configured to perform the present method including, but in no way limited to, thermally actuated inkjet dispensers, mechanically actuated inkjet dispensers, electrostatically actuated inkjet dispensers, magnetically actuated dispensers, piezoelectrically actuated dispensers, continuous inkjet dispensers, etc. Additionally, the ink-jet material dispenser can be heated to assist in dispensing the edible, optically invisible ink. Moreover, the present edible, invisible ink can be distributed using any number of printing processes including, but in no way limited to, inkjet printing, lithography, screen printing, gravure, and flexo printing.

The material reservoir (230) that is fluidly coupled to the inkjet material dispenser (250) houses the present edible, non-UV illuminating ink (260) prior to printing. The material reservoir may be any sterilizeable container configured to hermetically seal the edible, non-UV illuminating ink (260) prior to printing and may be constructed of any number of materials including, but in no way limited to metals, plastics, composites, or ceramics. Moreover, the material reservoir (230) may be an off-axis or on-axis component. According to one exemplary embodiment, the material reservoir (230) forms an integral part of the moveable carriage (240).

The pharmaceutical product (270) illustrated in FIG. 2 may be any number of pharmaceutical products and/or medicinal dosages configured to receive identifiable markings according to the present system and method. According to one exemplary embodiment, the pharmaceutical product (270) illustrated in FIG. 2 is made of a UV fluorescing material. Alternatively, because most pharmaceutical products are not UV-fluorescing materials, the pharmaceutical product (270) may include a coating made of a UV-fluorescing material including edible substances as defined above. By providing a pharmaceutical product (270) having a UV-fluorescing coating, the addition of a non-UV fluorescing image will selectively quench the fluorescence of the pharmaceutical product (270) thereby producing a viewable fluorescence contrast when viewed under UV light as explained in further detail below.

FIG. 2 also illustrates the components of the present system that facilitate reception of the edible, non-UV illuminating ink (260) on the pharmaceutical product (270). As shown in FIG. 2, a substrate (280) may transport and/or positionally secure a pharmaceutical product (270) during a printing operation. The formation and composition of the edible, non-UV illuminating ink (260) will now be described in further detail below.

Exemplary Composition

The edible, non-UV illuminating ink (260) illustrated in FIG. 2 is configured to provide an edible yet optically invisible ink that may be selectively deposited on a UV illuminating pharmaceutical or substrate so as to form a viewable image contrast upon the application of ultraviolet (UV) light. According to one exemplary embodiment, the present edible, non-UV illuminating ink (260) includes at least two main components: an ink vehicle and a colorant.

The ink vehicle component of the present edible, non-UV illuminating ink (260) provides a liquid solution that facilitates dispersion and dissolution of the colorant while enabling the selectively controlled transport of the colorant from an inkjet material dispenser (250) to a pharmaceutical product (270) or other ink receiving substrate. Additionally, the ink vehicle can also act as a binder to affix the colorant to the pharmaceutical product (270) or other print receiving substrate. The components of the ink vehicle may be made of any edible, non-UV fluorescing compound having invisible properties when viewed under normal white light conditions. Invisibility under normal white light conditions may be due to an optical transparency of the ink vehicle component, or a similarity in color between the ink component and underlying pharmaceutical or substrate. Examples of appropriate edible compounds are listed in the Generally Regarded as Safe (GRAS) list sponsored by the food and drug administration (FDA). According to one exemplary embodiment, the ink vehicle includes at least a solvent, but may also include additives configured to enhance various properties and characteristics of the resulting ink. Property enhancing additives that may form a part of the ink vehicle may include, but are in no way limited to, surfactants, buffers, and/or humectants.

The solvent component of the ink vehicle is included in the present edible, non-UV illuminating ink (260) for dispersion and transport of the colorant as well as any additives. The vehicle solvent imparts a jettable viscosity to the edible, non-UV illuminating ink (260) while also evaporating at a rate sufficient to cause a printed image to be resistant to smudging or smearing soon after it is deposited on a pharmaceutical product (270) or other ink receiving substrate. According to one exemplary embodiment, the solvent comprises water, thus creating a water-based vehicle. In addition to low cost, water is effective as a solvent for many additives, greatly reduces inkjet dispenser compatibility issues, effectively suspends colorants, and effectively controls drying rates of the ink. More specifically, a water-based vehicle may comprise from 20% by volume water up to about 90% by volume water. In another exemplary embodiment, the solvent component of the ink vehicle includes a mixture of water and an alcohol, such as ethyl alcohol. The addition of an alcohol to a solvent affects the viscosity and drying rate of the ink vehicle, as well as acting as a surfactant.

Surfactants and emulsifiers may be added to the solvent component of the present edible, non-UV illuminating ink (260) in order to facilitate dispersion and/or dissolution of the colorant and any other additive in the solvent. Typically, an edible alcohol may be used as the vehicle surfactant including, but in no way limited to, ethyl alcohol, glycerol, methyl alcohol, isopropyl alcohol, and butyl alcohol. Ethyl alcohol, for example, decreases the surface tension of water, thereby allowing a colorant and other additives to dissolve and/or disperse throughout the water more easily. The ethyl alcohol may also facilitate the jettability of the present edible, non-UV illuminating ink (260). Moreover, other edible compounds besides alcohols may also be used as a surfactant or emulsifier, including, but in no way limited to, lecithin, crillet, polyoxyethylene sorbitan monostearate (TWEEN), xanthan gum, sorbitol, and starches such as maize starch, corn starch, and potato starch. According to one exemplary embodiment, a surfactant or emulsifier may be present in a concentration of up to about 20% by volume of the ink vehicle. In one particular exemplary embodiment, the surfactant or emulsifier comprises ethyl alcohol in a concentration of about 10% to about 20% by weight of the vehicle.

A humectant may also be included in the present ink vehicle to control the moisture content and viscosity of the resulting edible, non-UV illuminating ink (260). The ink vehicle typically dries by evaporation once it is disposed on the pharmaceutical product (270) or other substrate surface; however, drying prior to printing decreases viscosity and thus may inhibit the jettability of the edible, non-UV illuminating ink (260). Additionally, drying prior to printing may alter a pharmaceutical concentration level of the edible, non-UV illuminating ink (260). Therefore, a humectant may be included in the vehicle to keep the edible, non-UV illuminating ink (260) from premature drying. The humectant may include, but is in no way limited to glycerin, sorbitol, mannitol, or any other edible humectant. According to one exemplary embodiment, the humectant can be present in the vehicle in a concentration of up to approximately 5% of the vehicle by volume. According to another exemplary embodiment, the humectant includes glycerin in a concentration of approximately 3% by volume, or about 4% by weight, of the ink vehicle.

According to one exemplary embodiment, the vehicle component of the present edible, invisible, non-UV fluorescing ink may also include other additives as needed including, but in no way limited to, driers, thinners, waxes, lubricants, reducing oils and solvents, body gum, binding varnish, antioxidants, anti-skinning agents, resins, and/or binders.

The present edible, non-UV illuminating ink (260) also includes an edible, invisible colorant component. The colorant component typically is not visible to the human eye when applied to the pharmaceutical product (270) or other substrate, either because it is colorless or because it is the same color as the pharmaceutical product (270) or substrate.

According to one exemplary method, an edible, invisible ink (260) was prepared using lecithin, ethyl alcohol, and water to form the vehicle, and acetaminophen as the colorant component. According to this exemplary embodiment, the vehicle component was prepared by combining 2% by volume of lecithin, 10% by volume of ethyl alcohol, and 88% by volume de-ionized water.

Additionally, as illustrated in FIG. 2, the pharmaceutical product (270) may include or be coated with a UV fluorescing colorant. Suitable colorants that may be used to coat the pharmaceutical product (270) or other substrate include any edible compounds, or combinations thereof, that naturally fluoresce when exposed to UV light including, but in no way limited to, riboflavin, riboflavin phosphate including riboflavin 5'-phosphate, pyridoxine hydrochloride, folic acid, quinine sulfate, niacin, nicotinamide, D&C Orange No. 5, or any appropriate combination thereof. The afore-mentioned fluorescent colorants may be applied to the surface of the pharmaceutical product (270) or other substrate by any known method including, but in no way limited to, ink jet spraying, rolling, dusting, etc.

According to one exemplary embodiment, the pharmaceutical product (270) or other substrate is coated by riboflavin or riboflavin phosphate in a concentration of up to approximately 9 milligrams per milliliter of coating vehicle, or up to approximately 1% by weight of the coating vehicle. In another exemplary embodiment, the coating vehicle comprises quinine sulfate in a concentration of up to approximately 1% by weight of the coating vehicle. The component concentrations mentioned above are merely given as examples and are in no way meant to limit the contemplated concentrations. Rather, the concentration of the colorant or the coating vehicle can be lower if less intense fluorescence is desired or higher if more intense fluorescence is desired.

Exemplary Composition Forming Methods

Figure 3:
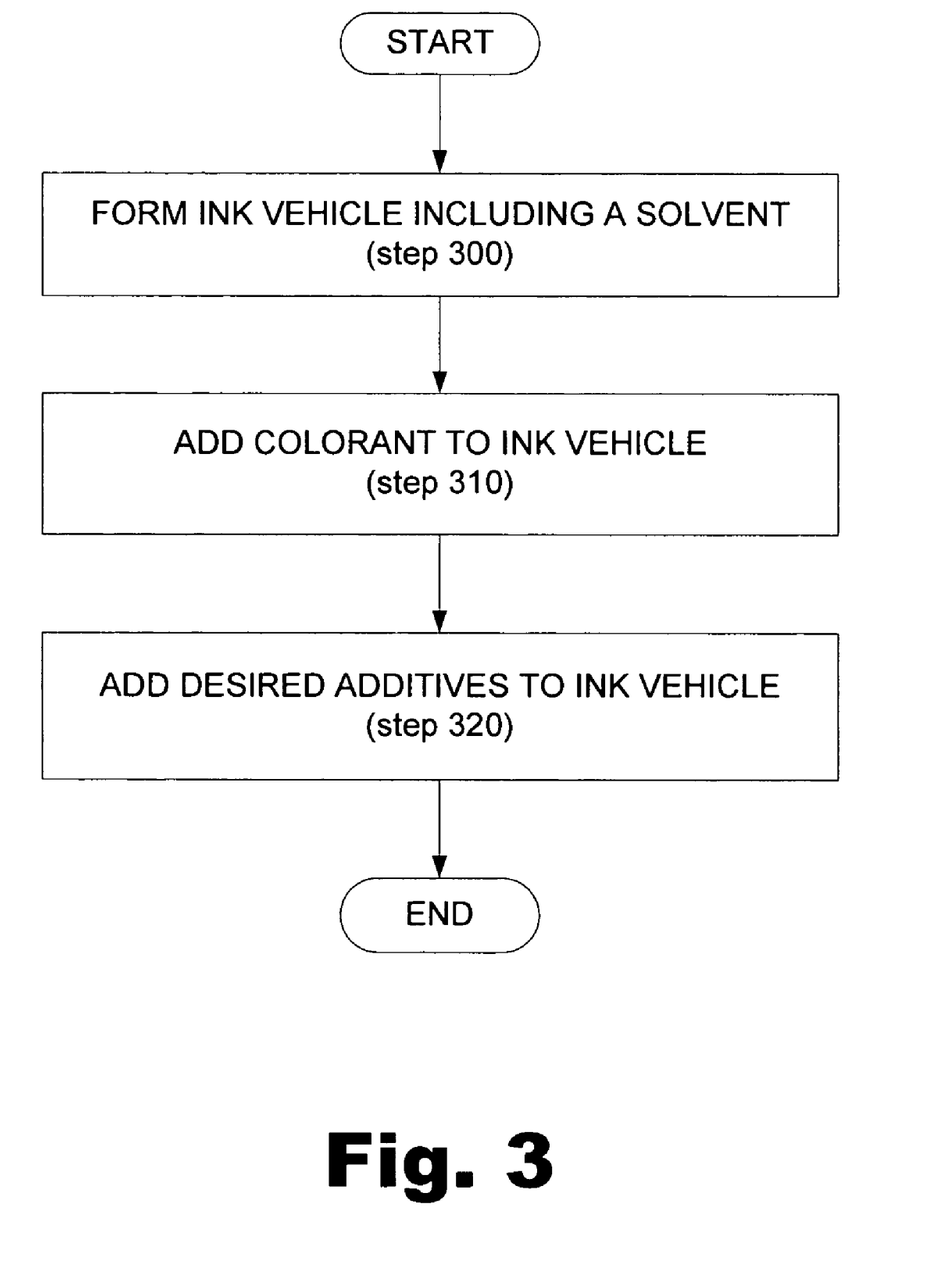
FIG. 3 is a flow chart illustrating a method for producing an ink used to form an edible, optically invisible image according to one exemplary embodiment.

FIG. 3 illustrates a method for forming the present edible, invisible, non-UV fluorescing ink (260; FIG. 2) according to one exemplary embodiment. The edible, non-UV fluorescing ink (260; FIG. 2) can be formed by a simple process of combining a solvent, colorant, and additives. As shown in FIG. 3, the present edible, invisible, non-UV fluorescing ink (260; FIG. 2) may be formed, according to one exemplary embodiment, by first forming an ink vehicle including a solvent (step 300). Once the ink vehicle is formed, a colorant may be added (step 310), followed by the optional addition of a number of desired additives (step 320). While FIG. 3 illustrates the additives being included in the present edible, invisible ink (260; FIG. 2) after the colorant is added (step 310), additives, such as a buffer, a humectant, a surfactant, or a pharmaceutical product can be added to the mixture before the colorant is added, after the colorant is added, or both.

According to one exemplary embodiment, the present edible, invisible ink can be made by performing the following steps: First, an aqueous acid or buffer solution is prepared. Colorant is then added to the acid solution and mixed. Next, a surfactant is added to the solution. Finally, the solution is mixed until the colorant is well dissolved. In another exemplary embodiment, the ink can be formed by performing the following steps: first, the ink vehicle is prepared by combining and mixing a solvent, surfactant, and humectant. The colorant is then added and mixed until dissolved.

The edible, invisible ink may be better understood in light of the following example. The example is merely intended to explain particular embodiments of the ink and are in no way intended to limit the ink to the compositions, processes, or methods described therein.

EXAMPLE

An edible, invisible, non-UV fluorescing ink may be prepared by performing the following steps. First, the vehicle is prepared by combining 10% v/v ethyl alcohol with 2% v/v lecithin and 88% v/v de-ionized water. Once the vehicle is formed, the colorant or other additive is added to the vehicle. According to this exemplary embodiment, 425 mg of acetaminophen is crushed and dissolved in a 35 mL of vehicle. The preparation is then filtered through a 0.45-micron mesh.

Exemplary Implementation and Operation

Figure 4:
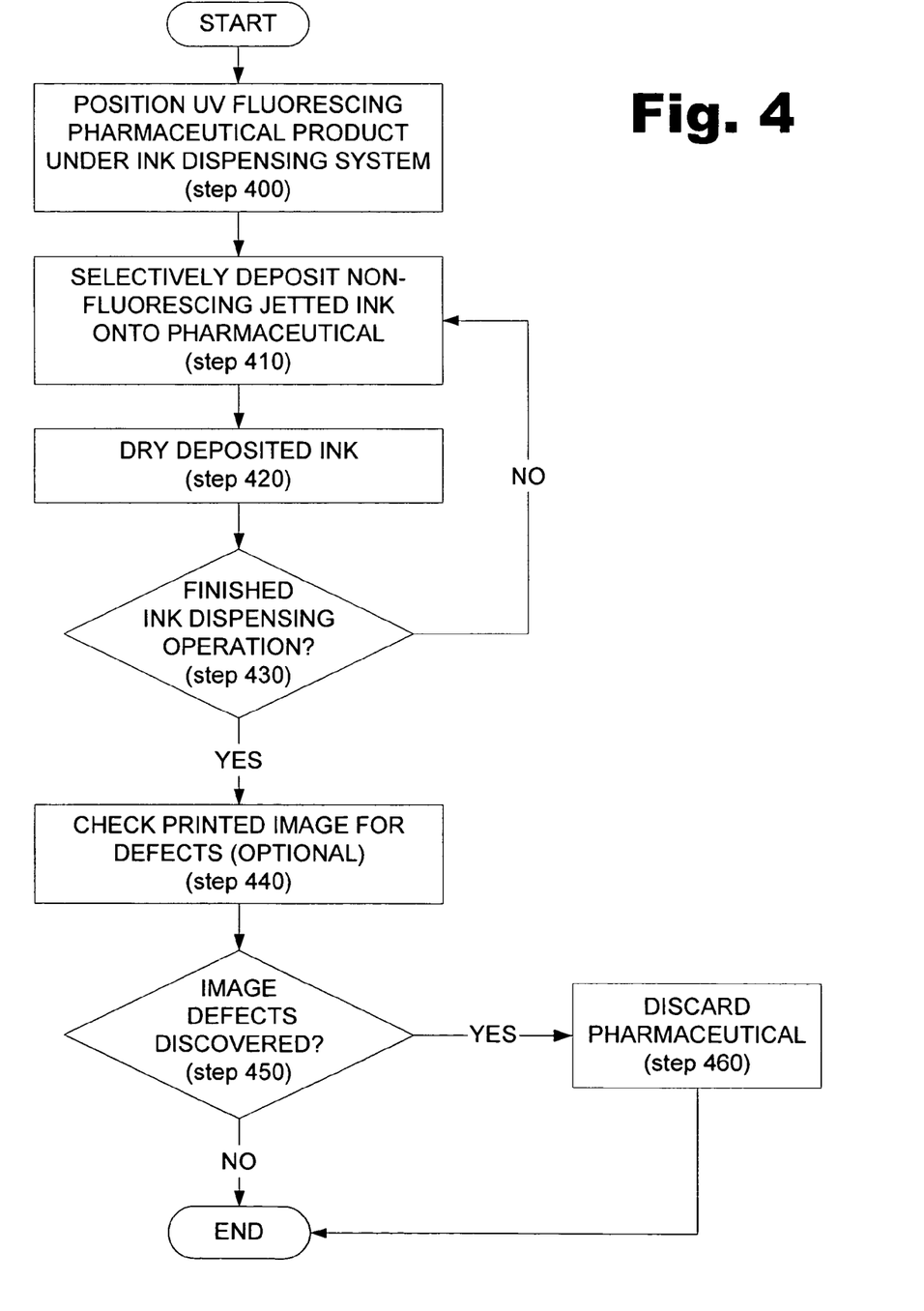
FIG. 4 is a flow chart illustrating a method for marking a pharmaceutical product with an edible, optically invisible image according to one exemplary embodiment.

Once formed, the present edible, invisible, non-UV fluorescing ink (260; FIG. 2) may be jetted onto a pharmaceutical product (270; FIG. 2) or other substrate to form a desired image that is invisible to the naked eye under normal white light conditions but generates a visibly fluorescing contrast that forms an image when exposed to UV light. FIG. 4 illustrates a method for implementing the present printing system (200; FIG. 2) to mark a pharmaceutical product with an edible, invisible, non-UV fluorescing ink (260; FIG. 2) according to one exemplary embodiment. As shown in FIG. 4, the present method begins by positioning a UV fluorescing pharmaceutical product under the present ink dispensing system (step 400). Once positioned, the ink dispensing system selectively deposits the edible, invisible, non-UV fluorescing ink onto the pharmaceutical product (step 410) where it subsequently dries (step 420). Upon deposition of the edible, invisible, non-UV fluorescing ink, a determination is made as to whether the present printing system (200; FIG. 2) has completed its ink dispensing operation (step 430). If it is determined that the ink dispensing operation is not complete (NO, step 430), the printing system again selectively deposits jetted ink onto the pharmaceutical product (step 410). If, however, the ink dispensing operation is complete (YES, step 430), the printed image is optionally examined for defects (step 440). If no defects are found (NO, step 450), the printing process is complete. If, however, printing defects are found on the printed image transferred to the pharmaceutical (YES, step 450), the pharmaceutical product may be discarded (step 460). The above-mentioned steps will now be described in further detail below.

As shown in FIG. 4, the present method for printing an edible, invisible ink on a pharmaceutical product begins by positioning a UV fluorescing pharmaceutical product to receive the edible, invisible, non-UV fluorescing ink under the ink dispensing system (step 400). As shown in FIG. 2, the UV fluorescing pharmaceutical product (270) may be positioned under the ink dispensing system (200) by a moveable substrate (280). Alternatively, an operator may manually place the UV fluorescing pharmaceutical product (270) adjacent to the ink dispensing system (200).

Once the UV fluorescing pharmaceutical product (270) is correctly positioned, the ink dispensing system (200) may be directed by the computing device (210) to selectively deposit the edible, non-UV illuminating ink (260) onto the pharmaceutical product (step 410; FIG. 4). As was mentioned previously, the image to be printed on the pharmaceutical product (270) may initially be developed on a program hosted by the computing device (210). The created image may then be converted into a number of processor accessible commands, which when accessed, may control the servo mechanisms (220) and the movable carriage (240) causing them to selectively emit edible, non-UV illuminating ink (260) onto the desired image. According to one exemplary embodiment, the edible, non-UV illuminating ink (260) may be emitted by the ink dispensing system (200) to form any number of images including, but in no way limited to, product names, product dosages, product identifying barcodes, or general product indicating shades. Precision and resolution of the resulting image may be varied by adjusting a number of factors including, but in no way limited to, the type of inkjet material dispenser (250) used, the distance between the inkjet material dispenser (250) and the pharmaceutical product (270), and the ink dispensing rate.

Once the edible, non-UV illuminating ink (260) has been selectively deposited onto the UV fluorescing pharmaceutical product (270) according to the desired image, the deposited ink may be dried to more securely affix the image to the pharmaceutical product (step 420; FIG. 4). When printed onto the pharmaceutical product (270) or other image receiving substrate, the colorant enters surface of the substrate, thereby preventing the ink from smudging. Moreover, the ink vehicle evaporates thereby binding or affixing the colorant to the pharmaceutical product (270) such that it is resilient to smudging in a short amount of time. Evaporation of the ink vehicle and affixation of the colorant may also occur more rapidly due to the addition of alcohols or driers in the ink vehicle, or the external application of thermal energy.

Upon deposition and subsequent drying, it is determined whether or not the ink dispensing operation has been completed on the UV fluorescing pharmaceutical product (step 430; FIG. 4). Completion of the ink dispensing operation may be evaluated by a system operator or by the coupled computing device (210). According to one exemplary embodiment, the computing device (210) determines whether sufficient edible, non-UV illuminating ink (260) has been dispensed to produce the desired image on the pharmaceutical product (270). If sufficient edible, non-UV illuminating ink (260) has not been dispensed (NO, step 430; FIG. 4), the ink dispensing system (200) continues to selectively deposit jetted ink onto the pharmaceutical product (step 410; FIG. 4). If, however, sufficient edible, non-UV illuminating ink (260) has been dispensed (YES, Step 430; FIG. 4), the dispensed image may optionally be checked for defects (step 440). Adequacy of the volume of edible, invisible, non-UV fluorescing ink dispensed may be evaluated by a number of flow-rate sensors (not shown) disposed on the inkjet material dispenser (250).

In order to check the dispensed image for defects (step 440; FIG. 4), the UV fluorescing pharmaceutical product (270) or other image receiving substrate may be exposed to a UV or other appropriate light source. According to one exemplary embodiment, the UV light may be any light with a wavelength between approximately 254 and 400 nanometers, or any light with a wavelength in the UV spectrum. Once the surface of the pharmaceutical product or other substrate is exposed to UV light, or another appropriate light, the surface of the UV fluorescing pharmaceutical product (270) or other UV fluorescing receiving substrate will fluoresce in the visible light range. In contrast to the UV fluorescing pharmaceutical product (270), the deposited edible, non-UV fluorescing ink (260) that has been selectively dispensed onto the surface of the pharmaceutical product will not fluoresce when exposed to the above-mentioned light source. Rather, according to one exemplary embodiment, the edible, non-UV fluorescing ink (260) will obscure the fluorescence of the pharmaceutical product (270) beneath the ink (260). The non-fluorescence of the edible, non-UV fluorescing ink (260) will generate an optically visible contrast that may then be scanned by an optical scanning device or optically viewed by a system operator to detect any image defects (step 440; FIG. 4). Defects may be detected by comparing the resulting image to the previously mentioned computer image.

According to one exemplary embodiment, if image defects are discovered (YES, step 450; FIG. 4), the pharmaceutical product may be discarded (step 460; FIG. 4) and the system adjusted. If, however, no image defects are discovered (NO, step 450; FIG. 4) the pharmaceutical product (270) may be subsequently packaged or otherwise distributed.

Figure 5A:
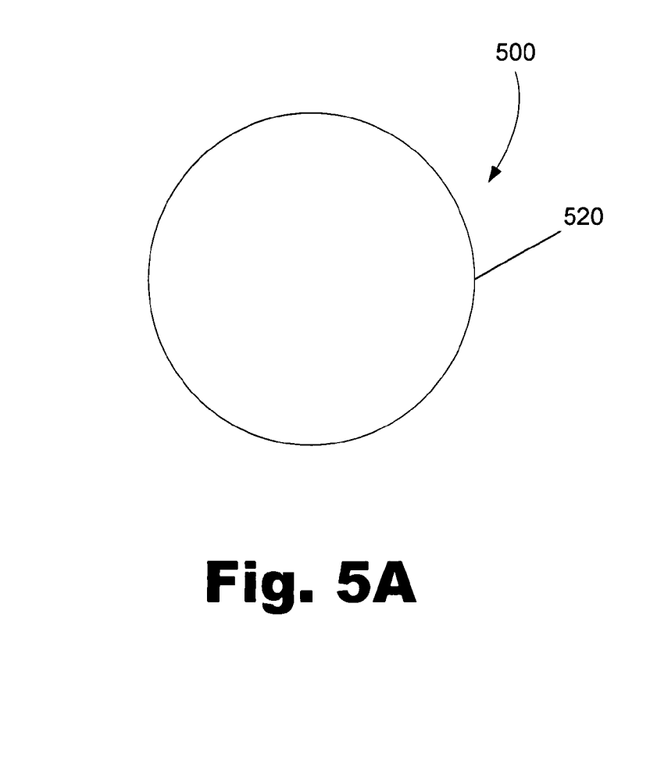
FIG. 5A is a perspective view illustrating a pharmaceutical product incorporating the present system and method when exposed to normal white light conditions according to one exemplary embodiment.

FIG. 5A illustrates a UV fluorescing pharmaceutical product (500) that has been processed according to the above-mentioned method when viewed under normal white light conditions according to one exemplary embodiment. As shown in FIG. 5A, a pill (520) or other pharmaceutical product (500) will not display any surface modifications or images when viewed under normal white light. This will maintain the aesthetic integrity of the pharmaceutical product (500).

Figure 5B:
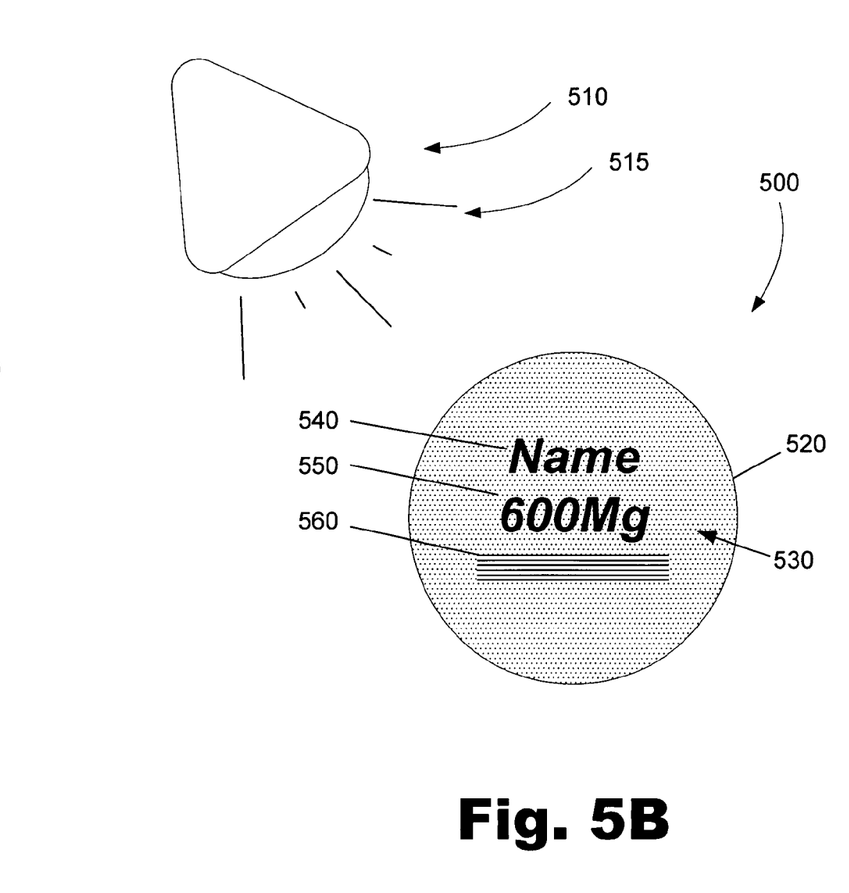
FIG. 5B is a perspective view illustrating a pharmaceutical product incorporating the present system and method when exposed to an ultraviolet light according to one exemplary embodiment.

FIG. 5B illustrates the pill (520) of FIG. 5A when viewed under UV light conditions. As shown in FIG. 5B, when a UV producing lamp (510) or other light source produces UV radiation (515), the UV fluorescing surface (530) of the pill (520) fluoresces. However, the edible, invisible, non UV fluorescing ink (260; FIG. 2) that has been disposed on the surface of the pill (520) or other pharmaceutical product (500) does not fluoresce in the visible range. Consequently, the areas of non-fluorescence provide a visible contrast that may be selectively formed as a product identifier. As shown in FIG. 5B, the present method may be used to produce a number of product identifiers including, but in no way limited to, product names (540), dosage indicators (550), and/or bar codes (560).

Marking pharmaceutical solid dosage forms with "invisible" information such as logos, names (540), and bar codes (560) will help track fraudulent dispensing of drugs, protect drugs from counterfeiting, and ensure that patients receive the right medication without affecting the product's appearance.

Additionally, dosage indicators (550), bar codes (560), and general surface hue or colors may be used by a pharmacist or pharmaceutical distributor to verify that all of the pharmaceuticals in a prescription or a shipment have equivalent dosages or chemistries. According to one exemplary embodiment, the means for verifying that all pharmaceuticals have equivalent dosages or chemistries includes retrieving information from a computer or database about a particular pharmaceutical by scanning a bar code (560) printed on the pharmaceutical. In another exemplary embodiment, the marked pharmaceuticals may be exposed to UV light (515) and then compared with a patient's medical record to ensure dispensing of the correct medicine.

Alternative Embodiments

Figure 6:
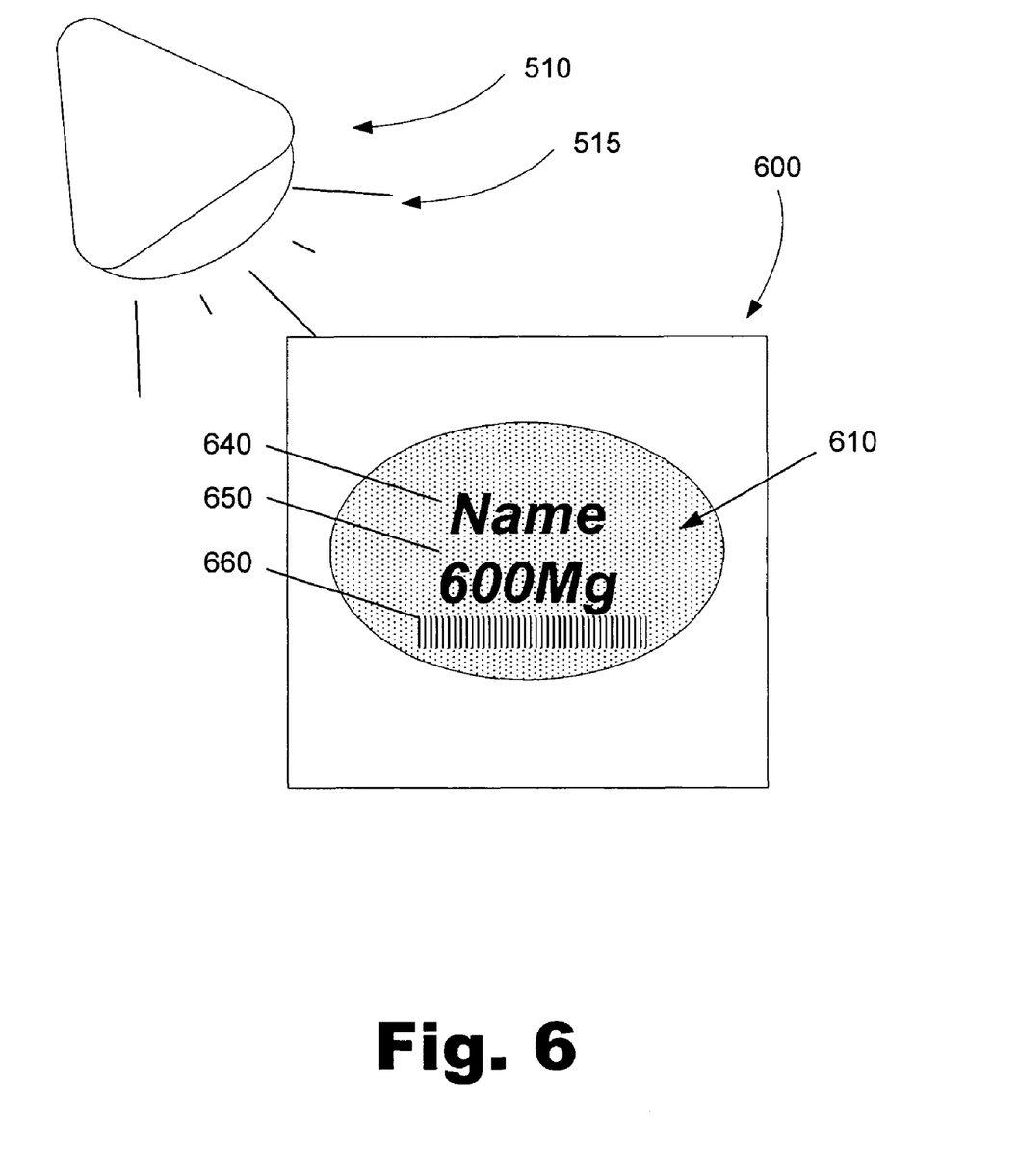
FIG. 6 is a top view of a pharmaceutical packaging incorporating the present system and method according to one exemplary embodiment.

In one exemplary alternative embodiment, the present edible invisible ink may be used to mark a urethane polymer covering or other pharmaceutical packaging as shown in FIG. 6. As is illustrated in FIG. 6, pharmaceuticals are often packaged in a urethane polymer covering (600) sometimes referred to as a blister coating. Similar to the restrictions placed on pharmaceuticals, the FDA restricts the colorants that may be used to mark pharmaceutical packaging. According to one exemplary embodiment, the present system and method is used to mark a urethane polymer covering (600) or other pharmaceutical covering with an edible, invisible, non-UV fluorescing ink (260; FIG. 2). According to this exemplary embodiment, a urethane polymer covering (600) or other pharmaceutical covering may first be coated with an FDA approved UV fluorescing material (610). Once the pharmaceutical covering is coated, a product name (640), dosage (650), barcode (660), and/or any other marking may be printed on the urethane polymer coating (600) with an edible non-UV fluorescing ink (260; FIG. 2) according to the methods explained above. Once printed, the edible, invisible, non-UV fluorescing ink (260; FIG. 2) will not obstruct the view of a contained pharmaceutical or otherwise deface the urethane polymer covering (600) when viewed under normal white light conditions. However, when exposed to UV light (515), the edible, invisible, non-UV fluorescing ink (260; FIG. 2) does not fluoresce in the visible light range, in contrast to the UV fluorescing coating (610). This contrast, when viewed under a UV light source, exposes the product name (640), dosage (650), barcode (660), and/or other marking printed on the urethane polymer covering (600) by the non-UV fluorescing ink (260; FIG. 2).

Figure 7:
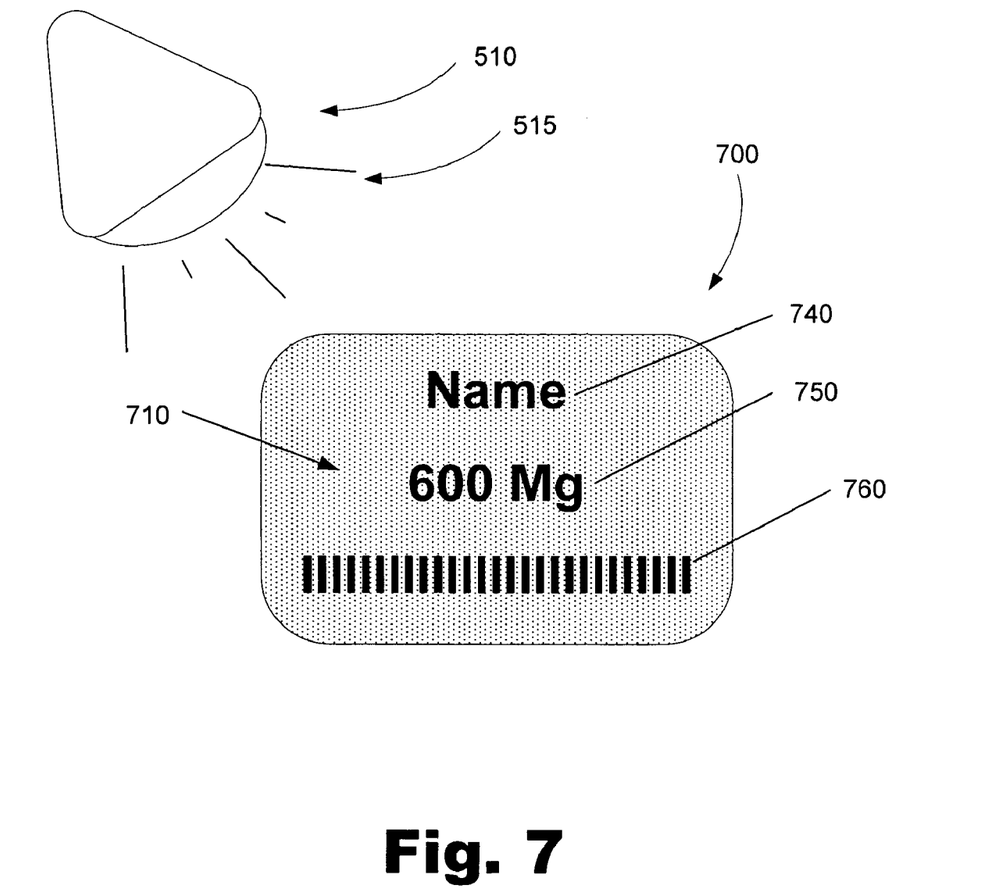
FIG. 7 is a top view illustrating an edible wafer marked with an edible, optically invisible ink containing a dosage of a pharmaceutical product according to one exemplary embodiment.

According to yet another exemplary alternative embodiment, illustrated in FIG. 7, the present edible, invisible, and non-UV fluorescing ink (260; FIG. 2) may also include a dosage of a pharmaceutical product. As illustrated in the system (700) of FIG. 7, a non-UV fluorescing ink (260; FIG. 2) containing a known concentration of medication is selectively printed onto an edible, UV fluorescing substrate (710). According to this exemplary embodiment, the UV fluorescing substrate (710) maybe any edible media including, but in no way limited to, cellulose, starch, or a wheat flour based media. Alternatively, the above-mentioned process may be performed on a non-UV fluorescing substrate (710) that has been coated with an edible, UV fluorescing coating as explained above. Due to the operational precision of thermal ink jets and other ink jet printing devices, a precise quantity of non-UV fluorescing ink (260; FIG. 2) containing a known concentration of medication may be selectively deposited on the UV fluorescing substrate (710) according to a specified dosage. Accordingly, the quantity of non-UV fluorescing ink (260; FIG. 2) used to form the requested dosage may be arranged to form a product name (740), a dosage indicator (750), and/or a barcode (760) as illustrated in FIG. 7.

The edible, non-UV fluorescing ink (260; FIG. 2) containing a known concentration of medication used to form the requested dosage illustrated in FIG. 7 may vary from the non-UV fluorescing ink illustrated above with reference to FIG. 2. According to one exemplary embodiment, the non-UV fluorescing ink (260; FIG. 2) containing a known concentration of medication includes at least two main components: a jettable vehicle and a known concentration of medication.

The ink vehicle component of the non-UV fluorescing ink (260; FIG. 2) containing a known concentration of medication provides an edible liquid solution that facilitates dispersion and dissolution of the medication while enabling the selectively controlled transport of the non-UV fluorescing medication from an inkjet material dispenser (250; FIG. 2) to a non-UV fluorescing substrate (710). Additionally, the edible ink vehicle can also act as a binder to affix the medication to the non-UV fluorescing substrate (710) and provide invisible properties when viewed under normal white light conditions. Invisibility under normal white light conditions may be due to an optical transparency of the ink vehicle component, or a similarity in color between the ink component and underlying pharmaceutical or substrate. According to one exemplary embodiment, the ink vehicle includes at least a solvent, but may also include additives configured to enhance various properties and characteristics of the resulting ink containing a known quantity of medication. Property enhancing additives that may form a part of the ink vehicle may include, but are in no way limited to, surfactants, buffers, and/or humectants as described above with reference to FIG. 2.

The solvent component of the ink vehicle is included in the present edible, non-UV illuminating ink (260; FIG. 2) containing a known quantity of medication for dispersion and transport of the medication as well as any additives. According to one exemplary embodiment, the solvent comprises water, thus creating a water-based vehicle. In another exemplary embodiment, the solvent component of the ink vehicle includes a mixture of water and an alcohol, such as ethyl alcohol. Surfactants and emulsifiers may also be added to the solvent component of the present edible, non-UV illuminating ink (260; FIG. 2) in order to facilitate dispersion and/or dissolution of the medication and any other additive in the solvent. A humectant may also be included in the present ink vehicle to control the moisture content and viscosity of the resulting edible, non-UV illuminating ink (260; FIG. 2) containing a known quantity of medication.

According to one exemplary embodiment, the vehicle component of the present edible, invisible, non-UV fluorescing ink containing a known quantity of medication may also include other additives as needed including, but in no way limited to, driers, thinners, waxes, lubricants, reducing oils and solvents, body gum, binding varnish, antioxidants, anti-skinning agents, resins, and/or binders.

Figure 8:
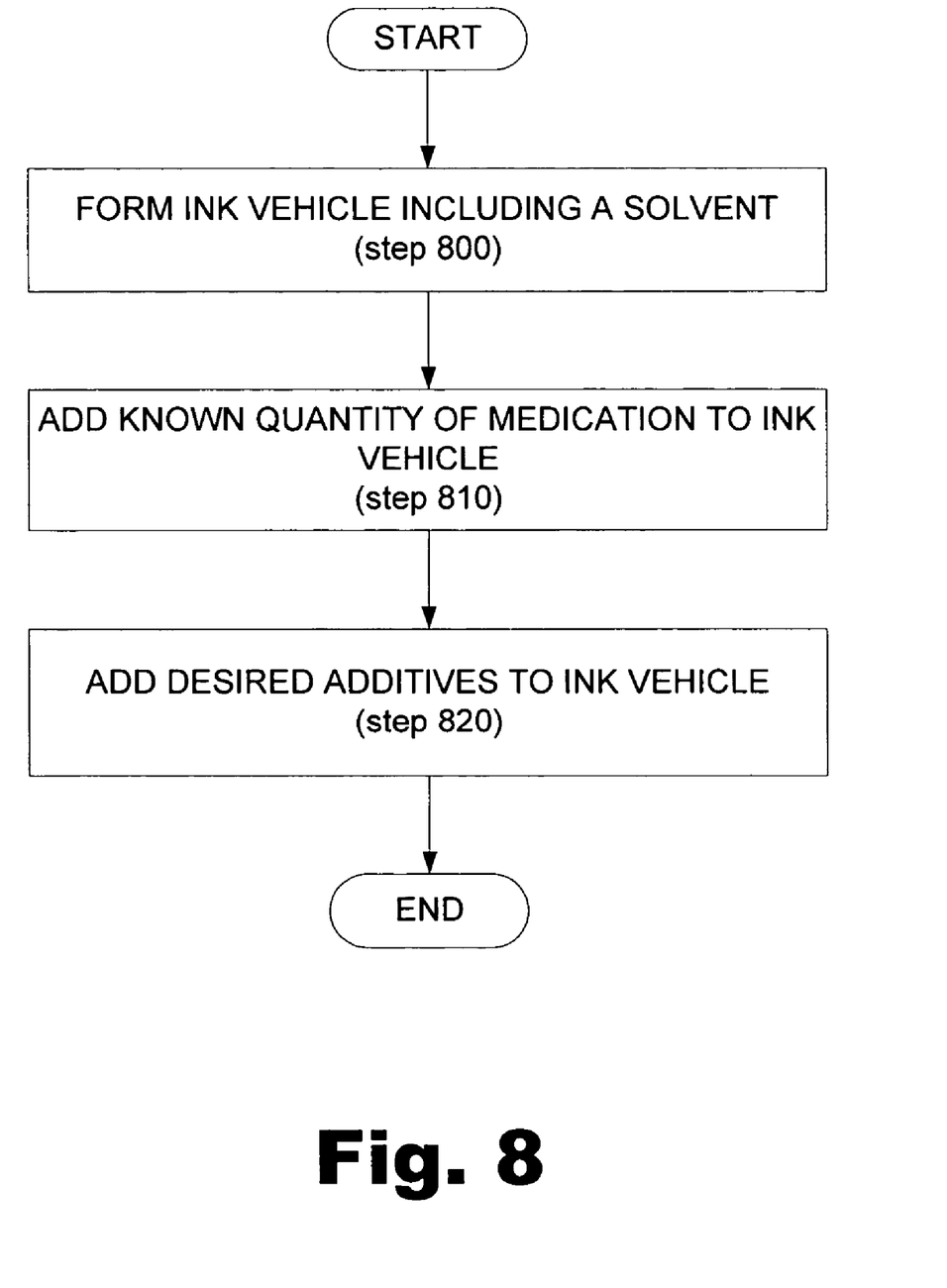
FIG. 8 is a flow chart illustrating a method of forming an edible, non-UV fluorescing ink containing a known medication according to one exemplary embodiment.

The present edible, non-UV illuminating ink (260; FIG. 2) containing a known quantity of medication may or may not include an edible, invisible colorant component. FIG. 8 illustrates one exemplary method for forming a non-UV illuminating ink (260; FIG. 2) containing a known quantity of medication and no colorant according to one exemplary embodiment. The exemplary non-UV illuminating ink (260; FIG. 2) containing a known quantity of medication can be formed by a simple process of combining a solvent, a known medication, and additives. As shown in FIG. 8, the exemplary non-UV illuminating ink (260; FIG. 2) containing a known quantity of medication may be formed, according to one exemplary embodiment, by first forming an ink vehicle including a solvent (step 800). Once the ink vehicle is formed, a known quantity of medication may be added (step 810). The solution may need to be stirred or otherwise agitated to dissolve the medication into the solvent. A number of desired additives may also be added to the solution (step 820) to impart any number of qualities to the solution. While FIG. 8 illustrates the additives being included in the present invisible ink (260; FIG. 2) after the medication is added (step 810), additives, such as a buffer, a humectant, or a surfactant can be added to the solution before the colorant is added, after the colorant is added, or both. Consequently, the order of performing the steps illustrated in FIG. 8 are not critical to the present system and method.

In conclusion, the present system and method for implementing an edible, invisible ink provide for the printing of information onto pharmaceutical products or other substrates in a manner that is "invisible" to the naked eye when viewed under normal white light conditions. However, when exposed to ultraviolet (UV) light between approximately 254 and 400 nanometers (nm), the surface of the pharmaceutical product or other substrate fluoresces in the visible light range (400-600 nm) while the edible, invisible ink does not, resulting in a visible contrast. The present edible, invisible ink may be safely used to print or otherwise mark on pharmaceutical substrates such as tablets, capsules, gel caps, pills, caplets, and other solid dosage forms; dental products and instruments; and or food products.

Products may be marked by the present edible, invisible ink with information such as, but not limited to, logos, names, bar codes, alphanumeric codes, text, watermarks, and other markings. Marking pharmaceuticals with information using invisible ink allows manufacturers and distributors to control fraudulent dispensing of drugs, control counterfeit production of drugs, and ensure that patients receive the correct medication, among other things.

Moreover, the present system and method may be used to precisely dispense a desired prescription of medicated ink onto an edible substrate. According to the present system and method, inkjet technology may be used to precisely dispense a dosage of medicated non-UV illuminating ink onto any edible UV illuminating substrate.

The preceding description has been presented only to illustrate and describe exemplary embodiments of the present system and method. It is not intended to be exhaustive or to limit the system and method to any precise form disclosed. Many modifications and variations are possible in light of the above teaching. It is intended that the scope of the system and method be defined by the following claims.

What is claimed is:

1. A pharmaceutical product or packaging comprising:
an ultraviolet (UV) fluorescing substrate; and
an invisible, edible, non-ultraviolet (UV) fluorescent ink comprising a jettable vehicle;
wherein said non-fluorescent ink is invisible when viewed in white light conditions; and
wherein said ink is selectively deposited onto said UV-fluorescing substrate, said ink selectively blocking fluorescence from said fluorescing substrate, thereby forming a UV viewable image on said substrate.

2. The pharmaceutical product or packaging of claim 1, wherein said substrate comprises a pharmaceutical product.

3. The pharmaceutical product or packaging of claim 1, wherein said substrate comprises a package for a pharmaceutical product.

4. The pharmaceutical product or packaging of claim 1, wherein said ink further comprises a known concentration of medication.

5. The pharmaceutical product or packaging of claim 4, wherein said substrate comprises a wafer made of one of a cellulose, a starch, or a wheat flour based medium.

6. The pharmaceutical product or packaging of claim 1, wherein said jettable vehicle comprises a solvent.

7. The pharmaceutical product or packaging of claim 6, wherein said solvent comprises one of water or an alcohol.

8. The pharmaceutical product or packaging of claim 6, wherein said jettable vehicle further comprises a surfactant.

9. The pharmaceutical product or packaging of claim 8, wherein said surfactant comprises one of an ethyl alcohol, a glycerol, a methyl alcohol, an ethyl alcohol, an isopropyl alcohol, a butyl alcohol, a lecithin, a crillet, a polyoxyethylene sorbitan monostearate, a xanthan gum, a sorbitol, or an edible starch.

10. The pharmaceutical product or packaging of claim 1, wherein said jettable vehicle further comprises an edible humectant.

11. The pharmaceutical product or packaging of claim 10, wherein said edible humectant comprises one of a glycerin, a sorbitol, or a mannitol.

12. The pharmaceutical product or packaging of claim 1, wherein said ink comprises a drug.

13. The pharmaceutical product or packaging of claim 1, wherein said jettable vehicle comprises:
lecithin;
ethyl alcohol; and
water.

14. The pharmaceutical product or packaging of claim 13, wherein said jettable vehicle further comprises:
approximately 10% v/v ethyl alcohol;
approximately 2% v/v lecithin; and
approximately 88% v/v water.

15. The pharmaceutical product or packaging of claim 12, wherein said drug comprises acetaminophen.

16. The pharmaceutical product or packaging claim 1, wherein said ink further comprises one of a drier, a thinner, a wax, a lubricant, a reducing oil, a solvent, a body gum, a binding varnish, an antioxidant, an anti-skinning agent, a resin, or a binder.

17. A printed medicinal dosage: comprising:
an edible, UV-fluorescing substrate; and
an invisible, edible, non-ultraviolet (UV) fluorescent ink, said ink comprising:
a jettable vehicle; and
a known drug concentration;
wherein said ink is selectively deposited onto said substrate to form a desired dosage of said drug, and selectively blocks said fluorescing substrate, thereby forming a UV viewable image on said substrate.

18. The printed medicinal dosage of claim 17, wherein said substrate comprises a wafer made of one of a cellulose, a starch, or a wheat flour based medium.

19. The printed medicinal dosage of claim 17, wherein said jettable vehicle comprises a solvent.

20. The printed medicinal dosage of claim 19, wherein said solvent comprises one of water or an alcohol.

21. The printed medicinal dosage of claim 19, wherein said jettable vehicle further comprises a surfactant.

22. The printed medicinal dosage of claim 21, wherein said surfactant comprises one of an ethyl alcohol, a glycerol, a methyl alcohol, an ethyl alcohol, an isopropyl alcohol, a butyl alcohol, a lecithin, a crillet, a polyoxyethylene sorbitan monostearate, a xanthan gum, a sorbitol, or an edible starch.

23. The printed medicinal dosage of claim 17, wherein said jettable vehicle further comprises an edible humectant.

24. The printed medicinal dosage of claim 23, wherein said edible humectant comprises one of a glycerin, a sorbitol, or a mannitol.

25. The printed medicinal dosage of claim 17, wherein said jettable vehicle comprises:
lecithin;
ethyl alcohol; and
water.

26. The printed medicinal dosage of claim 25, wherein said jettable vehicle further comprises:
approximately 10% v/v ethyl alcohol;
approximately 2% v/v lecithin; and
approximately 88% v/v water.

27. The printed medicinal dosage of claim 17, wherein said drug comprises acetaminophen.

28. The printed medicinal dosage of claim 17, wherein said ink further comprises one of a drier, a thinner, a wax, a lubricant, a reducing oil, a solvent, a body gum, a binding varnish, an antioxidant, an anti-skinning agent, a resin, or a binder.

29. A method for labeling a UV-fluorescing substrate comprising:
positioning said UV-fluorescing substrate adjacent to an inkjet material dispenser; and
selectively jetting an edible, invisible, non-UV fluorescing ink onto said UV-fluorescing substrate with said inkjet material dispenser;
wherein said edible, invisible, non-UV fluorescing ink comprises a jettable vehicle;
wherein said non-fluorescent ink is invisible when viewed in white light conditions; and
wherein said ink is configured to selectively block a fluorescence of said UV-fluorescing substrate when exposed to an ultraviolet light.

30. The method of claim 29, wherein said substrate comprises a pharmaceutical product.

31. The method of claim 30, wherein said pharmaceutical product comprises one of a tablet, a capsule, a gel cap, a pill, or a caplet.

32. The method of claim 29, wherein said substrate comprises one of a food product, a pharmaceutical covering, or a dental product.

33. The method of claim 29, wherein said inkjet material dispenser comprises one of a thermally actuated inkjet dispenser, a mechanically actuated inkjet dispenser, an electrostatically actuated inkjet dispenser, a magnetically actuated dispenser, a piezoelectrically actuated dispenser, or a continuous inkjet dispenser.

34. The method of claim 29, wherein said selectively jetting comprises:
forming a desired image on a program hosted by a computing device;
translating said desired image into a plurality of machine commands configured to control said inkjet material dispenser; and
causing said inkjet material dispenser to selectively dispense said edible, invisible, non-UV fluorescing ink onto said substrate in a pattern corresponding to said desired image.

35. The method of claim 34, wherein said desired image comprises a product identifiable mark.

36. The method of claim 35, wherein said product identifiable mark comprises one of a logo, a name, a bar code, a dosage indicator, a general surface hue, or a color.

37. The method of claim 29, wherein:
said ink further comprises a known concentration of a drug; and said UV fluorescing substrate comprises an edible UV-fluorescing substrate.

38. The method of claim 37, further comprising:
selectively dispensing said ink onto said edible UV-fluorescing substrate to form a desired dosage of said drug.

39. The method of claim 29, wherein said ultraviolet light comprises a wavelength between 254 and 400 nanometers.

40. A method for labeling a pharmaceutical product comprising:
coating said pharmaceutical product with a UV-fluorescing material;
positioning said pharmaceutical product adjacent to an inkjet material dispenser; and
selectively jetting an edible, invisible, non-UV fluorescing ink onto said pharmaceutical product with said inkjet material dispenser;
wherein said edible, invisible, non-UV fluorescing ink is configured to selectively block a fluorescence of said UV-fluorescing coating when exposed to an ultraviolet light.

41. The method of claim 40, wherein said selectively jetting an edible, invisible, non-UV fluorescing ink onto said pharmaceutical product comprises jetting said edible, invisible, non-UV fluorescing ink in the form of a desired image.

42. The method of claim 41, wherein said desired image comprises a product identifiable mark.

43. The method of claim 42, wherein said product identifiable mark comprises one of a logo, a name, a bar code, a dosage indicator, a general surface hue, or a color.

44. The method of claim 40, wherein said pharmaceutical product comprises one of a tablet, a capsule, a gel cap, a pill, a caplet, or a pharmaceutical covering.

45. A method for forming a dosage of a pharmaceutical product, comprising:
providing an edible, UV-fluorescing substrate; and
selectively dispensing an edible, non-UV fluorescing ink containing a known concentration of said pharmaceutical product onto said edible, UV-fluorescing substrate;
wherein an amount of said pharmaceutical product associated with said selective dispensing corresponds to said dosage.

46. The method of claim 45, wherein said edible, UV-fluorescing substrate comprises on of a cellulose, a starch, or a wheat flour based medium.

47. The method of claim 45, wherein said edible, UV-fluorescing substrate further comprises a coating of a naturally UV-fluorescing material.

48. The method of claim 45, wherein said selectively dispensing an edible, non-UV fluorescing ink comprises selectively dispensing said edible, non-UV fluorescing ink in a product identifiable mark.

49. The method of claim 48, wherein said product identifiable mark comprises one of a logo, a name, a number, a bar code, an alphanumeric code, a text, or a watermark.

50. The method of claim 45, wherein said selective dispensing is performed by one of a thermally actuated inkjet dispenser, a mechanically actuated inkjet dispenser, an electrostatically actuated inkjet dispenser, a magnetically actuated dispenser, a piezoelectrically actuated dispenser, or a continuous inkjet dispenser.

51. A method for tracking a fraudulent dispensing of pharmaceuticals, comprising:
coating said pharmaceutical with a UV-fluorescing material;
selectively marking said pharmaceutical with information in an edible, invisible, non-UV fluorescing ink, wherein said edible, invisible, non-UV fluorescing ink is configured to block the fluorescence of said UV-fluorescing material when exposed to an ultraviolet light; and
exposing said pharmaceutical to said ultraviolet light.

52. The method of claim 51, wherein said exposing said pharmaceutical to said ultraviolet light comprises verifying said information.

53. The method of claim 51, wherein:
said marking comprises forming a barcode on said pharmaceutical; and
said verifying said information comprises scanning said barcode.

54. A method for controlling an administration of proper medication to patients, comprising:
coating said medication with a UV-fluorescing material;
marking said medication with information in an edible, invisible, non-UV fluorescing ink, wherein said edible, invisible, non-UV fluorescing ink is configured to selectively block a fluorescence of said coating when exposed to an ultraviolet light; and
exposing said pharmaceutical to said ultraviolet light to verify said information.

55. A pharmaceutical comprising:
a surface;
a UV-fluorescing coating disposed on said surface;
wherein said UV-fluorescing coating is marked with an edible, invisible, non-UV fluorescing ink;
said edible, invisible, non-UV fluorescing ink being configured to selectively block a fluorescence of said coating when exposed to an ultraviolet light.

56. The pharmaceutical of claim 55, wherein said pharmaceutical comprises one of a tablet, a capsule, a gel cap, a caplet, or a pill.

57. The pharmaceutical of claim 55, wherein said mark comprises information regarding said pharmaceutical.

58. The pharmaceutical of claim 55, wherein said mark comprises one of a logo, a name, a number, a bar code, an alphanumeric code, a text, or a watermark.

59. The pharmaceutical of claim 55, wherein said edible, invisible, non-UV fluorescing ink is distributed onto said coating by one of a thermally actuated inkjet dispenser, a mechanically actuated inkjet dispenser, an electrostatically actuated inkjet dispenser, a magnetically actuated dispenser, a piezoelectrically actuated dispenser, or a continuous inkjet dispenser.

60. A system for labeling a pharmaceutical comprising:
a pharmaceutical carrying substrate, in which said pharmaceutical carrying substrate is an edible, UV-fluorescing substrate;
an edible, invisible, non-UV fluorescing ink;
an inkjet material dispenser disposed adjacent to said pharmaceutical carrying substrate that dispenses said ink; and
an ink reservoir coupled to said inkjet material dispenser that supplies said ink to said inkjet material dispenser;
in which said edible, invisible, non-UV fluorescing ink selectively blocks a fluoresce in a visible range when exposed to an ultraviolet light.

61. The system of claim 60, further comprising:
a computing device controllably coupled to said inkjet material dispenser;
wherein said computing device is configured to control a selective dispensing of said edible, invisible, non-UV fluorescing ink by said inkjet material dispenser.

62. The system of claim 60, wherein said inkjet material dispenser comprises one of a thermally actuated inkjet dispenser, a mechanically actuated inkjet dispenser, an electrostatically actuated inkjet dispenser, a magnetically actuated dispenser, a piezoelectrically actuated dispenser, or a continuous inkjet dispenser.

63. A method for preventing a counterfeiting of pharmaceuticals, comprising marking identification information on a UV-fluorescing pharmaceutical with an edible, invisible, non-UV fluorescing ink, wherein said edible, invisible, non-UV fluorescing ink is configured to selectively block a fluoresce in a visible range when exposed to an ultraviolet light.

64. The method of claim 63, further comprising exposing said pharmaceutical to said ultraviolet light.

65. The method of claim 64, wherein said exposing said pharmaceutical to said ultraviolet light comprises verifying said identification information.

66. The method of claim 63, wherein:
said marking comprises forming a barcode on said pharmaceutical; and
said verifying said information comprises scanning said barcode.

* * * * *

UNITED STATES PATENT AND TRADEMARK OFFICE
CERTIFICATE OF CORRECTION

PATENT NO. : 8,080,097 B2
APPLICATION NO. : 10/946883
DATED : December 20, 2011
INVENTOR(S) : Vanessa I. Chinea et al.

Page 1 of 1

It is certified that error appears in the above-identified patent and that said Letters Patent is hereby corrected as shown below:

In column 13, line 37, in Claim 16, delete "packaging claim" and insert -- packaging of claim --, therefor.

In column 13, line 42, in Claim 17, delete "dosage:" and insert -- dosage --, therefor.

Signed and Sealed this
Twentieth Day of November, 2012

David J. Kappos
*Director of the United States Patent and Trademark Office*